United States Patent [19]
McCarthy et al.

[11] Patent Number: 5,922,745
[45] Date of Patent: Jul. 13, 1999

[54] COMPOSITION AND METHOD FOR INHIBITING THE GROWTH OF MICROORGANISMS INCLUDING STABILIZED SODIUM HYPOBROMITE AND ISOTHIAZOLONES

[75] Inventors: Robert E. McCarthy, Naperville; Anthony W. Dallmier, Aurora; William F. McCoy, Naperville, all of Ill.

[73] Assignee: Nalco Chemical Company, Naperville, Ill.

[21] Appl. No.: 08/963,397

[22] Filed: Nov. 3, 1997

[51] Int. Cl.$^6$ .......................... A01B 43/78; A01B 43/80; A01B 25/00; A01B 59/00

[52] U.S. Cl. .......................... 514/372; 514/365; 424/405; 424/723

[58] Field of Search .................................. 514/365, 372; 424/723, 405

[56] References Cited

U.S. PATENT DOCUMENTS

| | | | |
|---|---|---|---|
| 4,295,932 | 10/1981 | Pocius | 162/161 |
| 4,427,435 | 1/1984 | Lorenz et al. | 71/67 |
| 4,539,071 | 9/1985 | Clifford et al. | 162/161 |
| 4,595,691 | 6/1986 | LaMarre et al. | 514/367 |
| 4,661,503 | 4/1987 | Martin et al. | 514/372 |
| 4,906,651 | 3/1990 | Hsu | 514/372 |

FOREIGN PATENT DOCUMENTS

| | | |
|---|---|---|
| WO 96/14092 | 5/1996 | WIPO . |
| WO 97/34827 | 9/1997 | WIPO . |

OTHER PUBLICATIONS

Dallmier et al., (CA 127:295339, abstract of WO 970925), 1997.

"Mixtures of Quaternary Ammonium Compounds and Long–chain Fatty Acids as Antifungal Agents", Applied Microbiology, F.C. Kull, P.C. Eisman, H.D. Sylwestrowicz, R.L. Mayer, 9:538–541 (1961).

"Threshold Levels for Bromate Formation in Drinking Water", Water Supply, vol. 13, No. 1, Paris, pp. 157–167, 1995.

"Toxicity and Risk Assessment of Bromate", Water Supply, vol. 13, No. 1, Paris, pp. 29–33, 1995.

*Primary Examiner*—Jose' G. Dees
*Assistant Examiner*—Sabiha N. Qazi
*Attorney, Agent, or Firm*—Kelly L. Cummings; Thomas M. Breininger

[57] ABSTRACT

A synergistic composition and method for inhibiting microbiological growth which comprises a combination of stabilized sodium hypobromite with a mixture of 5-chloro-2-methyl 4-isothiazolin-3-one and 2-methyl-4-isothiazolin-3-one.

12 Claims, No Drawings

COMPOSITION AND METHOD FOR INHIBITING THE GROWTH OF MICROORGANISMS INCLUDING STABILIZED SODIUM HYPOBROMITE AND ISOTHIAZOLONES

FIELD OF THE INVENTION

The invention is a composition for controlling microbiological growth which comprises a combination of stabilized sodium hypobromite with a mixture of 5-chloro-2-methyl-4-isothiazolin-3-one and 2-methyl-4-isothiazolin-3-one.

The invention is also a method for controlling microbiological growth which comprises a combination of stabilized sodium hypobromite with a mixture of 5-chloro-2-methyl-4-isothiazolin-3-one and 2-methyl-4-isothiazolin-3-one.

BACKGROUND OF THE INVENTION

The proliferation of microorganisms and the resultant formation of slime is a problem which commonly occurs in aqueous systems. Problematic slime producing microbes may include: bacteria, fungi, and algae. Slime deposits typically occur in many industrial aqueous systems including cooling water systems, pulp and paper mill systems, petroleum operations, clay and pigment slurries, recreational water systems, air washer systems, decorative fountains, food, beverage, and industrial process pasteurizers, sweet-water systems, gas scrubber systems, latex systems, industrial lubricants, cutting fluids, etc.

Biocides and antimicrobials are used to control or eliminate microbial growth in a number of different aqueous media. If left untreated, microbes and microbial biofilms (slimes) can cause deterioration of cooling tower structures, loss in heat exchange efficiency in a cooling system, aesthetic defects in decorative fountains, promotion and acceleration of corrosion on metal surfaces, increased down time, or breaks in paper sheets in pulp and paper systems. Bacterial slimes may also be objectionable as they relate to cleanliness and sanitation in breweries, dairies, and other industrial food and beverage process water systems. The proliferation of microbial contamination in lubricants and cutting fluids is a common problem due to the elevated temperatures and unsanitary conditions found in many metal working plants. As a consequence of the deleterious effects of uncontrolled microbial growth and contamination in many industrial processes, different antimicrobials have been developed to aid in eliminating and controlling microbial growth.

Often, one antimicrobial (biocide) is insufficient to control microbial growth in the aqueous media. Biocides may act in combination, i.e. synergistically, to yield better antimicrobial performance as opposed to the efficacy obtained when each biocide is used separately. Biocides may act on the target microbe in a number of different ways to cause cell stress or death. The mechanisms by which biocides exert antimicrobial activity depend upon a number of factors which include the chemical properties of the antimicrobial, and the biochemical and physical characteristics of the target microbe. Some biocides target the cell membrane or cell wall. Others target critical enzymes or the cellular metabolic machinery which leads to cell death or disruption of cellular replication.

The combination of two biocides may yield enhanced efficacy beyond the cumulative or additive effect of the two biocides. This likely reflects a synergistic anti-microbial effect on some essential component(s) of the cell for survival and sustained growth. A combination of two biocides that are synergistic allows for the addition of lesser amounts of the individual biocides to achieve the desired level of microbial control. This has both advantageous environmental and economic impacts. It allows for reduced discharge of potential environmental pollutants and a more cost effective control program for these diverse industrial systems.

For this invention, the methylchloro/methylisothiazoline biocide is a broad spectrum antimicrobial agent that is widely used in industrial systems to control algae, bacteria, and fungi. Commercial preparations of the compound for use as a cooling tower biocide (KATHON® WT; a microbial control agent available from Rohm and Haas Company, Philadelphia, Pa.) are water-based formulations of inorganic stabilizers and active ingredients. The active ingredients, 5-chloro-2-methyl-4-isothiazolin-3-one and 2-methyl-4-isothiazolin-3-one, are present in the approximate ratio of 3:1.

Isothiazolones are effective against many microorganisms. The microbiocidal activity of isothiazolones is likely due to their electrophilic nature and their interaction with certain key enzymes such as cellular dehydrogenases as well as the pronounced effect they have on cellular respiration.

It was shown in previous research that isothiazolones can be used to achieve significant disinfection of a bacterial biofilm, but it is not a good agent to remove adherent biofilm. Conversely, stabilized sodium hypobromite may act as a penetrant, and disrupt adhered biomass. Therefore, the persistence of isothiazolones coupled with the reactivity and the biofilm removal properties of stabilized sodium hypobromite yields an antimicrobial composition with superior performance compared to the results obtained when either biocide is used independently. Also, the combination of these two biocides clearly exerts an enhanced (synergistic) antimicrobial effect on planktonic microorgansims as indicated in the data shown herein. The exact mechanism for this observed synergy remains unknown.

It is an object of the present invention to provide novel antimicrobial compositions which provide enhanced effectiveness for controlling or inhibiting the growth of microorganisms in aqueous systems. It is another object of this invention to provide an improved method for controlling microorganisms in aqueous systems. It is an advantage of the present invention that the biocidal compositions permit a reduction in the amount of biocide required to achieve acceptable microbiological control.

Important applications of the synergistic antimicrobial compositions of the present invention include but are not limited to inhibiting the growth of bacteria and fungi in aqueous media. The composition of the present invention possesses unexpected synergistic activity against microorganisms, including bacteria and fungi.

Stabilized sodium hypobromite is less volatile and more stable than other halogenated molecules such as sodium hypochlorite and sodium hypobromite. Also, much higher levels of available halogen for microbial disinfection are attained using stabilized sodium hypobromite than with other halogenated antimicrobials. Bromate formation is significantly reduced with the use of stabilized sodium hypobromite (1997, Dallmier, A. W. and W. F. McCoy. PCT Int. Appl., WO 97/34827). The United States EPA identified some health concerns relevant to bromate formation (1995, Amy, G. et al. Water Supply. 13(1):157). Animal carcinogenesis has been linked to low bromate levels in drinking water (1995, Fawell, J. K. and G. O'Neill. Water Supply. 13(1):29). Further, stabilized sodium hypobromite yielded reduced generation of adsorbable organic halogen (AOX) in laboratory studies and process waters.

Stabilized sodium hypobromite yields significant reduction of viable microbial populations at concentrations between 1.0 and 2.0 ppm total residual oxidant (as chlorine). The isothiazolone mixture (1.5% active ingredients) is typically used at concentrations of 100 to 200 ppm as product to obtain similar reductions in microbial populations. This invention provides superior microbiological control by combining stabilized sodium hypobromite with a mixture of 5-chloro-2-methyl-4-isothiazolin-3-one and 2-methyl-4-isothiazolin-3-one. The combination of the two antimicrobials allows for significantly less use of either antimicrobial compared to the necessary amount of each individual antimicrobial to achieve the same biocidal performance.

As is well known in the art, isothiazolines exhibit synergistic antimicrobial properties when combined with certain other biocides. Synergistic blends of 5-chloro-2-methyl-4-isothiazolin-3-one and 2-methyl-4-isothiazolin-3-one with glutaraldehyde were disclosed in U.S. Pat. No. 4,539,071; with dodecyl guanidine hydrochloride disclosed in U.S. Pat. No. 4,661,503; and with 2-(thiocyanomethylthio)-benzothiazole disclosed in U.S. Pat. No. 4,595,691. The Pocius reference (U.S. Pat. No. 4,295,932) discloses a synergistic composition of isothiazolones with either chlorine or chlorine dioxide. Microbiocidal compositions containing halogen-releasing compounds are disclosed in WO 96/14092. However, the synergistic biocidal composition described herein was not disclosed or suggested by the above-mentioned references.

SUMMARY OF THE INVENTION

A synergistic biocidal blend of stabilized sodium hypobromite with a mixture of 5-chloro-2-methyl-4-isothiazolin-3-one and 2-methyl-4-isothiazolin-3-one.

DETAILED DESCRIPTION OF THE PREFERRED EMBODIMENTS

The present invention provides, under one embodiment, for inhibiting the growth of microorganisms in industrial fluids, a composition which comprises a combination of stabilized sodium hypobromite and a mixture of 5-chloro-2-methyl-4-isothiazolin-3-one and 2-methyl-4-isothiazolin-3-one. This composition may be utilized in a method to control microbiological growth.

For the practice of this invention, the microbiological growth may be selected from the group consisting of bacteria, fungi, algae, and combinations thereof. The stabilized sodium hypobromite may be sodium hypobromite stabilized with sodium sulfamate. The sodium hypobromite may be stabilized with an alkali metal sulfamate, such as sodium sulfamate. Moreover, the sodium hypobromite may also be stabilized with an acid amide derivative selected from the group consisting of: carbonic acids, hydrogen cyanide, carboxylic acids, amino acids, sulfuric acids, phosphoric acids, and boric acids.

The method is applicable to industrial fluids selected from the group consisting of recirculating cooling waters; food, beverage and industrial process waters; paper mill systems; brewery pasteurizers; air washer systems; oil field drilling fluids and muds; heat transfer systems, and decorative fountains, among others. The amount of stabilized sodium hypobromite may range from about 0.05 ppm to about 10 ppm, total residual oxidant, and the amount of the mixture of 5-chloro-2-methyl-4-isothiazolin-3-one and 2-methyl-4-isothiazolin-3-one ranges from about 0.05 ppm to about 6.0 ppm, active ingredient.

The composition and method may be used for controlling bacteria in recirculating cooling waters wherein the weight ratio of said mixtures to stabilized sodium hypobromite is from about 1.0:10.0 to about 10.0:1.0; for controlling fungi in recirculating cooling waters wherein the weight ratio of said mixtures to stabilized sodium hypobromite is from about 1.0:10.0 to about 10.0:1.0; for controlling algae in recirculating cooling waters wherein the weight ratio of said mixtures to stabilized sodium hypobromite is from about 1.0:10.0 to about 10.0:1.0; for controlling bacteria in paper mill systems wherein the weight ratio of said mixtures to stabilized sodium hypobromite is from about 1:10 to about 10:1.

When the method is utilized for controlling microbial growth, the pH of said recirculating cooling water may be controlled within a range of about 2.5 to about 11.0. More preferably, the pH may be controlled within the range of about 6.0 to about 10.

The composition includes a sufficient amount of either biocide to obtain acceptable microbiological control in an aqueous system (an effective antimicrobial amount). A typical industrial use concentration of the stabilized sodium hypobromite would range from about 0.05 to about 10 ppm total residual oxidant (as chlorine) and a typical use concentration of the isothiazolone mixture would range from about 0.05 to 6.0 ppm, as active ingredient (active ingredient refers to the amount of isothiazolones in the aqueous solution). Total residual oxidant as used herein is defined as hypohalite or hypohalous acid including chemical combinations of those two compounds with ammonia or organic nitrogen-containing compounds.

Important applications of the synergistic antimicrobial compositions of the present invention include but are not limited to inhibiting the growth of bacteria, fungi, and algae in cooling water systems, sweetwater systems, gas scrubber systems, pulp and paper mill systems, controlling microbial contamination and deposits in oil field drilling fluids and muds, petroleum recovery processes, controlling bacterial and fungal growth in clay and pigment slurries, latex systems, air washer systems, and food, beverage and industrial process pasteurizers.

The mixture of isothiazolones utilized for the practice of this invention is commercially available as a 1.5% actives aqueous solution and includes a mixture of 5-chloro-2-methyl-4-isothiazolin-3-one and 2-methyl-4-isothiazolin-3-one. As used herein, the term "stabilized sodium hypobromite" indicates NaOBr stabilized with sodium sulfamate. However, NaOBr can be stabilized with other stabilizers which includes the acid amide derivatives of: carbonic acids, hydrogen cyanide, carboxylic acids, amino acids, sulfuric acids, phosphoric acids, and boric acids. Moreover, stabilizers can be selected from the group of compounds having an N—H or $NH_2$ group adjacent to an electron withdrawing functional group such as C=O, S=O, P=O, or B=O.

Stabilization of NaOBr is desirable to prevent disproportionation into halates and halides upon storage. As a result of stabilization, these biocides can be stored more safely since less bromate is generated, fewer organic molecules containing halogens are formed, and volatility is reduced. A stabilized aqueous alkali or alkaline earth metal hypobromite solution may be prepared in the following fashion:

a. Mixing an aqueous solution of alkali or alkaline earth metal hypochlorite having from about 5 percent to about 70 percent available halogen as chlorine with a water soluble bromide ion source;

b. Allowing the bromide ion source and the alkali or alkaline earth metal hypochlorite to react to form a 0.5 to 70 percent by weight aqueous solution of unstablized alkali or alkaline earth metal hypobromite;

c. Adding to the unstabilized solution of alkali or alkaline earth metal hypobromite an aqueous solution of an alkali metal sulfamate in a quantity to provide a molar ratio of alkali metal sulfamate to alkali or alkaline earth metal hypobromite from about 0.5 to about 7; and d. Recovering a stabilized aqueous alkali or alkaline earth metal hypobromite solution.

The stabilized sodium hypobromite utilized herein is available from Nalco Chemical Company of Naperville, Ill. under the trade name of STABREX.

The synergistic composition of this invention may be added separately to an industrial system or may be formulated as a simple mixture comprising its essential ingredients.

It may be the case that the stabilized sodium hypobromite will act synergistically when combined with other non-oxidizing biocides. It is expected that the above detailed description would also apply to the composition and method for other non-oxidizing biocides. Examples of other non-oxidizing biocides are glutaraldehyde, 2,2-dibromo-3-nitrilopropionamide (DBNPA), alkyldimethylbenzylammonium chloride (ADBAC), dimethyl dialkyl ammonium chloride, methylenebisthiocyanate (MBT), 2-decylthioethanamine (DTEA), tetrakishydroxymethyl phosphonium sulfate (THPS), dithiocarbamate, cyanodithioimidocarbonate, 2-methyl-5-nitroimidazole-1-ethanol, 2-(2-bromo-2-nitroethenyl) furan (BNEF), beta-bromo-beta-nitrostyrene (BNS), beta-nitrostyrene (NS), beta-nitrovinyl furan (NVF), 2-bromo-2-bromomethyl-glutaronitrile (BBMGN), bis(trichloromethyl) sulfone, S-(2-hydroxypropyl)thiomethanesulfonate, tetrahydro-3,5-dimethyl-2H-1,3,5-hydrazine-2-thione, 2-(thiocyanomethylthio)benzothiazole (TCTMB), 2-bromo-4'-hydroxyacetophenone, 1,4-bis(bromoacetoxy)-2-butene, bis(tributyltin) oxide (TBTO), copper sulfate, 2-(tert-butylamino)-4-chloro-6-(ethylamino)-s-triazine, dodecylguanidine acetate and dodecylguanadine hydrochloride (DGH).

The following examples are presented to describe the preferred embodiments and utilities of the invention and are not meant to limit the invention unless otherwise stated in the claims appended hereto.

EXAMPLE ONE

The efficiency of the invention was tested in the following manner. *Pseudomonas aeruginosa* was grown overnight in L-broth, then washed, and resuspended in sterile synthetic cooling water consisting of 150 ppm calcium, 75 ppm magnesium, and 110 ppm alkalinity at a pH of approximately 8.0. For the assay, 20 ml of sterile synthetic cooling water were added per test tube. 0.25 ml of the washed bacterial suspension and the indicated amount of biocide were added to the appropriate test tubes. After an 18 hour contact time with the biocides, the cells were serially diluted and spread plated onto tryptone glucose extract agar (Difco; Detroit, Mich.). Plates were incubated at 37° C. for 24 hours, then scored for viable counts. Viable bacterial counts are reported as colony forming units (CFU/ml).

Synergism was determined by an industrially accepted method as described by Kull, F. C., Eisman, P. C., Sylwestrowicz, H. D. and Mayer, R. L. in *Applied Microbiology*, 9:538–541 (1961), using the equation for the calculation of a synergy index determined by:

$$\frac{Qa}{QA} + \frac{Qb}{QB} = \text{SynergyIndex (S.I.)}$$

wherein

QA=concentration of compound A in parts per million (ppm) acting alone, which produced an endpoint;

Qa=concentration of compound A in ppm, in the mixture, which produced an endpoint;

QB=concentration of compound B in ppm acting alone which produced an endpoint;

Qb=concentration of compound B in ppm, in the mixture, which produced an endpoint.

When the sum of Qa/QA and Qb/QB is greater than 1.0, antagonism is indicated. When the sum is equal to 1.0, additivity is indicated, and when the sum is less than 1.0, synergy is demonstrated.

TABLE I

| Biocide | Biocide Amount (ppm) | Bacterial Count[1] (CFU/mL) | Synergy Index | Synergy Rating |
|---|---|---|---|---|
| None | None | 16,000,000 | | |
| A | 0.25 | 10,800,000 | | |
| A | 0.50 | 4,300,000 | | |
| A | 0.75 | 400,000 | | |
| A | 1.0 | 20,000 | | |
| A | 2.0 | 3,000 | | |
| B | 20 | 5,300,000 | | |
| B | 40 | 1,100,000 | | |
| B | 80 | 530,000 | | |
| B | 160 | 90,000 | | |
| A/B | 0.25/20 | 120,000 | | |
| A/B | 0.25/40 | 120,000 | | |
| A/B | 0.25/80 | 40,000 | | |
| A/B | 0.25/160 | 5,000 | | |
| A/B | 0.50/20 | 33,000 | | |
| A/B | 0.50/40 | 3,000 | 0.75 | Yes |
| A/B | 0.50/80 | 1,400 | 0.75 | Yes |
| A/B | 0.50/160 | 60 | | |
| A/B | 0.75/20 | 24,000 | | |
| A/B | 0.75/40 | 5,000 | 0.63 | Yes |
| A/B | 0.75/80 | 3,200 | 0.88 | Yes |
| A/B | 0.75/160 | 30 | | |

A = STABREX ™, stabilized sodium hypobromite, available from Nalco Chemical Company, Naperville, IL. Biocide measured as ppm total residual oxidant.
B = Mixture of 5-chloro-2-methyl-4-isothiazolin-3-one and 2-methyl-4-isothiazolin-3-one (1.5% active ingredients, available from Rohm and Haas Company, Philadelphia, PA). Biocide measured as ppm product.
[1]= measurement taken at 18 hours; at initial time (t = 0), bacterial count = 8,000,000 CFU/ml.

EXAMPLE TWO

The procedure described in Example One was utilized to obtain the results in Table II. However, for this example, the test inoculum was a mixed population of cooling water bacteria obtained from an operating cooling tower in the Midwest region of the United States. Synergy was indicated.

TABLE II

| Biocide | Biocide Amount (ppm) | Bacterial Count[1] (CFU/mL) | Synergy Index | Synergy Rating |
|---|---|---|---|---|
| None | None | 22,000,000 | | |
| A | 0.5 | 16,000,000 | | |
| A | 0.75 | 8,100,000 | | |
| A | 1.0 | 2,400,000 | | |
| A | 2.0 | 19,000 | | |
| B | 25 | 500,000 | | |
| B | 50 | 100,000 | | |
| B | 100 | 900,000 | | |
| B | 200 | 130,000 | | |
| A/B | 0.5/25 | 300,000 | | |
| A/B | 0.5/50 | 37,000 | | |
| A/B | 0.5/75 | 70,000 | | |
| A/B | 0.5/100 | 600 | 0.75 | Yes |
| A/B | 0.75/25 | 5,000 | 0.51 | Yes |

TABLE II-continued

| Biocide | Biocide Amount (ppm) | Bacterial Count[1] (CFU/mL) | Synergy Index | Synergy Rating |
|---|---|---|---|---|
| A/B | 0.75/50 | 3,000 | 0.63 | Yes |
| A/B | 0.75/75 | 300 | 0.76 | Yes |
| A/B | 0.75/100 | 900 | 0.88 | Yes |
| A/B | 1.0/25 | 1,000 | 0.63 | Yes |
| A/B | 1.0/50 | 100 | 0.75 | Yes |
| A/B | 1.0/75 | <100 | 0.88 | Yes |
| A/B | 1.0/100 | <10 | | |

A = STABREX ™, stabilized sodium hypobromite, available from Nalco Chemical Company, Naperville, IL. Biocide measured as total residual oxidant.
B = Mixture of 5-chloro-2-methyl-4-isothiazolin-3-one and 2-methyl-4-isothiazolin-3-one (1.5% actives, available from Rohm & Haas Company, Philadelphia, PA). Biocide measured as ppm product.
[1]= measurement taken at 18 hours; at initial time (t = 0), bacterial count = 11,000,000 CFU/ml.

EXAMPLE THREE

The procedure described in Example One was utilized to obtain the results in Table III. Sulfamic acid is not considered biocidal. Therefore, no endpoint could be determined nor a synergy index calculated. These data indicate that there is no synergy between sulfamic acid and the isothiazolones mixture.

TABLE III

| Chemical | Amount (ppm) | Bacterial Count[1] (CFU/mL) |
|---|---|---|
| None | None | 34,000,000 |
| C | 0.5 | 32,000,000 |
| C | 1 | 26,000,000 |
| C | 2 | 23,000,000 |
| C | 4 | 38,000,000 |
| C | 8 | 38,000,000 |
| C | 10 | 32,000,000 |
| B | 20 | 1,900,000 |
| B | 40 | 1,200,000 |
| B | 80 | 160,000 |
| B | 160 | 40,000 |
| B | 200 | 20,000 |
| C/B | 0.5/20 | 1,600,000 |
| C/B | 0.5/40 | 4,400,000 |
| C/B | 0.5/80 | 250,000 |
| C/B | 0.5/160 | 200,000 |
| C/B | 1.0/20 | 4,700,000 |
| C/B | 1.0/40 | 2,600,000 |
| C/B | 1.0/80 | 250,000 |
| C/B | 1.0/160 | 20,000 |
| C/B | 2.0/20 | 3,900,000 |
| C/B | 2.0/40 | 700,000 |
| C/B | 2.0/80 | 200,000 |
| C/B | 2.0/160 | 43,000 |

B = Mixture of 5-chloro-2-methyl-4-isothiazolin-3-one and 2-methyl-4-isothiazolin-3-one (1.5% actives, available from Rohm & Haas Company, Philadelphia, PA). Biocide measured as ppm product.
C = Sulfamic acid, available from PMC Specialty Group, Inc., Rocky River, Ohio.
[1]= measurement taken at 16 hours; at initial time (t = 0), bacterial count = 12,700,000 CFU/ml.

EXAMPLE FOUR

The following procedure was utilized to obtain the results of Table IV. The test organism *Candida guillermondii* (yeast) was grown overnight in L-broth at 30° C., then washed, and resuspended in sterile synthetic cooling water (pH 8.0) consisting of 150 ppm calcium, 75 ppm magnesium, and 110 ppm alkalinity.

To perform the assay, yeast cells were exposed to the test biocides and spread plated onto acidified potato dextrose agar (Difco; Detroit, Mich.). Plates were incubated for two days at 30° C., and viable colony counts were recorded. All counts are expressed as viable yeast cells recovered as CFU/ml. Synergy was indicated.

TABLE IV

| Biocide | Biocide Amount (ppm) | Yeast Count[1] (CFU/mL) | Synergy Index | Synergy Rating |
|---|---|---|---|---|
| None | None | 700,000 | | |
| A | 0.25 | 190,000 | | |
| A | 0.5 | 900,000 | | |
| A | 1.0 | 100,000 | | |
| A | 2.0 | 80,000 | | |
| B | 5.0 | 20,000 | | |
| B | 10.0 | 40,000 | | |
| B | 20.0 | 1,100 | | |
| B | 40.0 | 100 | | |
| B | 50.0 | 100 | | |
| A/B | 0.25/5 | 30,000 | | |
| A/B | 0.25/10 | 20,000 | | |
| A/B | 0.25/20 | 100 | 0.63 | Yes |
| A/B | 0.25/40 | <100 | | |
| A/B | 0.50/5 | 32,000 | | |
| A/B | 0.50/10 | 8,000 | 0.75 | Yes |
| A/B | 0.50/20 | 200 | 0.75 | Yes |
| A/B | 0.50/40 | <100 | | |

A = STABREX ™, stabilized sodium hypobromite, available from Nalco Chemical Company, Naperville, IL. Biocide measured as ppm total residual oxidant.
B = Mixture of 5-chloro-2-methyl-4-isothiazaolin-3-one and 2-methyl-4-isothiazolin-3-one (1.5% actives, available from Rohm and Haas Company, Philadelphia, PA). Biocide measured as ppm product.
[1]= measurement taken at 17 hours; at initial time (t = 0), yeast count = 210,000 CFU/ml.

EXAMPLE FIVE

Biocidal capabilities of the treating agents were also tested using a pulp and paper mill mixed bacterial population. A pulp and paper white water sample at a pH of 5.5 containing a mixed a bacterial population was taken from a Midwestern U.S. pulp and paper mill.

The test protocol described in Example One was utilized. The results are detailed in Table V. Synergy was indicated.

TABLE V

| Biocide | Biocide Amount (ppm) | Bacterial Count[1] (CFU/mL) | Synergy Index | Synergy Rating |
|---|---|---|---|---|
| None | None | 10,000,000 | | |
| A | 2.5 | 1,200,000 | | |
| A | 5.0 | 250,000 | | |
| A | 10.0 | 100,000 | | |
| A | 20.0 | 8,000 | | |
| B | 25.0 | 13,000 | | |
| B | 50.0 | 10,000 | | |
| B | 100.0 | 8,000 | | |
| B | 200.0 | 8,000 | | |
| A/B | 2.5/25 | 3,000 | 0.38 | Yes |
| A/B | 2.5/50 | 8,000 | 0.63 | Yes |
| A/B | 2.5/100 | 5,000 | | |
| A/B | 2.5/200 | 5,000 | | |
| A/B | 5.0/25 | 15,000 | | |
| A/B | 5.0/50 | 1,000 | 0.75 | Yes |
| A/B | 5.0/100 | 1,000 | | |
| A/B | 5.0/200 | 9,000 | | |

A = STABREX ™, stabilized sodium hypobromite, available from Nalco Chemical Company, Naperville, IL. Biocide measured as ppm total residual oxidant.
B = Mixture of 5-chloro-2-methyl-4-isothiazolin-3-one and 2-methyl-4-isothiazolin-3-one (1.5% actives, available from Rohm & Haas Company, Philadelphia, PA). Biocide measured as ppm product.
[1]= measurement taken at 19 hours; at initial time (t = 0), aerobic bacterial count = 1,900,000 CFU/ml

EXAMPLE SIX

The procedure described in Example One was utilized to obtain the results of Table VI. Synergy was indicated.

TABLE VI

| Biocide | Biocide Amount (ppm) | Bacterial Count[1] (CFU/mL) | Synergy Index | Synergy Rating |
|---|---|---|---|---|
| None | None | 50,000,000 | | |
| D | 0.5 | 18,000 | | |
| D | 1.0 | 1,300 | | |
| D | 2.0 | <100 | | |
| D | 4.0 | <10 | | |
| D | 6.0 | <10 | | |
| B | 25.0 | 3,500,000 | | |
| B | 50.0 | 700,000 | | |
| B | 100.0 | 520,000 | | |
| B | 200.0 | 50,000 | | |
| D/B | 0.5/25 | <100 | 0.38 | Yes |
| D/B | 0.5/50 | <1,000 | 0.50 | Yes |
| D/B | 0.5/100 | <100 | 0.75 | Yes |
| D/B | 0.5/200 | <100 | | |
| D/B | 1.0/25 | <1,000 | | |
| D/B | 1.0/50 | <100 | 0.75 | Yes |
| D/B | 1.0/100 | <100 | | |
| D/B | 1.0/200 | <100 | | |

B = Mixture of 5-chloro-2-methyl-4-isothiazolin-3-one and 2-methyl-4-isothiazolin-3-one (1.5% actives, available from Rohm & Haas Company, Philadelphia, PA). Biocide measured as ppm product.
D = Hypobromous acid was prepared from a solution of elemental bromine obtained from Aldrich Chemcial Co., Milwaukee, WI. Biocide measured as ppm total residual oxidant.
[1] = measurement taken at 17 hours; at initial time (t = 0), aerobic bacterial count = 10,000,000 CFU/ml.

Changes can be made in the composition, operation and arrangement of the method of the present invention described herein without departing from the concept and scope of the invention as defined in the following claims:

We claim:

1. A composition for controlling microbiological growth in industrial fluids which comprises a combination of stabilized sodium hypobromite with a mixture of 5-chloro-2-methyl-4-isothiazolin-3-one and 2-methyl-4-isothiazolin-3-one.

2. The composition of claim 1 wherein said microbiological growth is selected from the group consisting of bacteria, fungi, algae, and combinations thereof.

3. The composition of claim 1 wherein said stabilized sodium hypobromite is sodium hypobromite stabilized with sodium sulfamate.

4. The composition of claim 3 wherein said sodium hypobromite is stabilized with an alkali metal sulfamate.

5. The composition of claim 3 wherein said sodium hypobromite is stabilized with an acid amide derivative selected from the group consisting of: carbonic acids, hydrogen cyanide, carboxylic acids, amino acids, sulfuric acids, phosphoric acids, and boric acids.

6. The composition of claim 1 wherein said industrial fluids are selected from the group consisting of cooling waters; food, beverage and industrial process waters; pulp and paper mill systems; brewery pasteurizers; sweetwater systems; air washer systems; oil field drilling fluids and muds; petroleum recovery processes; industrial lubricants; cutting fluids; heat transfer systems; gas scrubber systems; latex systems; clay and pigment systems; and decorative fountains.

7. The composition of claim 1 wherein the amount of stabilized sodium hypobromite ranges from about 0.05 ppm to about 10 ppm, total residual oxidant, and the amount of the mixture of 5-chloro-2-methyl-4-isothiazolin-3-one and 2-methyl-4-isothiazolin-3-one ranges from about 0.05 ppm to about 6.0 ppm active ingredients.

8. The composition of claim 1 for controlling bacteria in recirculating cooling waters wherein the weight ratio of said mixtures to stabilized sodium hypobromite is from about 1.0:10.0 to about 10.0:1.0.

9. The composition of claim 1 for controlling fungi in recirculating cooling waters wherein the weight ratio of said mixtures to stabilized sodium hypobromite is from about 1.0:10.0 to about 10.0:1.0.

10. The composition of claim 1 for controlling algae in recirculating cooling waters wherein the weight ratio of said mixtures to stabilized sodium hypobromite is from about 1.0:10.0 to about 10.0:1.0.

11. The composition of claim 1 for controlling bacteria in paper mill systems wherein the weight ratio of said mixtures to stabilized sodium hypobromite is from about 1:10 to about 10:1.

12. A composition for controlling microbiological growth in industrial fluids which comprises a combination of stabilized sodium hypobromite with a compound selected from the group consisting of: glutaraldehyde, 2,2-dibromo-3-nitrilopropionamide, 2-bromo-2-nitropropane-1,3 diol, 1-bromo-1-(bromomethyl)-1,3-propanedicarbonitrile, tetrachloroisophthalonitrile, alkyldimethylbenzylammonium chloride, dimethyldialkyl ammonium chloride, poly(oxyethylene(dimethyliminio)ethylene(diemethyliminio) ethylene dichloride, methylene bisthiocyanate, 2-decylthiothanamine, tetrakishydroxymethyl phosphonium sulfate, dithiocarbamate, cyanodithioimidocarbonate, 2-methyl-5-nitroimidazole-1-ethanol, 2-(2-bromo-2-nitroethenyl)furan, beta-bromo-beta-nitrostyrene, beta-nitrostyrene, beta-nitrovinyl furan, 2-bromo-2-bromomethyl glutaronitrile, bis(trichloromethyl) sulfone, S-(2-hydroxypropyl)thiomethanesulfonate, tetrahydro-3,5-dimethyl-2H-1,3,5-hydrazine-2-thione, 2-(thiocyanomethylthio)benzothiazole, 2-bromo-4'-hydroxyacetophenone, 1,4-bis(bromoacetoxy)-2-butene, bis(tributyltin)oxide, copper sulfate, 2-tertbutylamino)-4-chloro-6-(ethylamino)-s-triazine, dodecylguanidine acetate and acetate dodecylguanidine hydrochloride.

* * * * *